United States Patent [19]

Nayak

[11] Patent Number: 5,447,930
[45] Date of Patent: Sep. 5, 1995

[54] TOPICAL ANESTHETIC COMPOSITIONS

[75] Inventor: Ammunje S. Nayak, Great Meadows, N.J.

[73] Assignee: Warner-Lambert Company, Morris Plains, N.J.

[21] Appl. No.: 58,503

[22] Filed: May 6, 1993

[51] Int. Cl.$^6$ ............................................. A61K 31/535
[52] U.S. Cl. .................................. 514/239.2; 544/174
[58] Field of Search ......................... 514/232; 544/174

[56] References Cited

U.S. PATENT DOCUMENTS

| | | | |
|---|---|---|---|
| 2,870,151 | 1/1959 | Wright et al. | 424/642 |
| 4,389,418 | 6/1983 | Burton | 424/365 |
| 4,937,078 | 6/1990 | Mezei et al. | 424/450 |
| 4,963,591 | 10/1990 | Fourman et al. | 514/944 |
| 5,002,974 | 3/1991 | Geria | 514/782 |
| 5,013,545 | 5/1991 | Blackman et al. | 424/81 |
| 5,081,158 | 1/1992 | Pomerantz | 514/781 |

*Primary Examiner*—C. Warren Ivy
*Assistant Examiner*—Zinna N. Davis
*Attorney, Agent, or Firm*—Jean B. Barish

[57] ABSTRACT

An improved, clear and non-greasy topical anesthetic for the relief of various skin irritations such as minor burns, insect bites, rashes and allergic reactions is prepared using pramoxine hydrochloride and zinc acetate as the active ingredients.

6 Claims, No Drawings

TOPICAL ANESTHETIC COMPOSITIONS

FIELD OF INVENTION

The present invention relates generally to an improved topical anesthetic for the temporary relief of pain and irritation of the skin resulting from minor burns, insect bites, allergic reactions and the like. The topical medication is a clear liquid and therefore unnoticeable and undetectable by others when applied.

BACKGROUND OF THE INVENTION

Topical anesthetics are widely used agents that are absorbed by the skin and temporarily block nerve endings that perceive inflammation and other skin injury. The active agent is generally incorporated in an oil-based carrier comprising a lotion or liquid that is poured and spread over the skin in a thin layer or sprayed thereon using a pump or pressurized aerosol formulation. Many topical aesthetic agents are known, perhaps the most widely used being lidocaine, prilocaine, xylocaine, benzocaine and the like. These may be combined with one another in a form of dual relief action or also combined with other agents such a antihistamines, anti-inflammatory agents or antiseptic compositions for multiple action relief.

U.S. Pat. No. 5,013,545 to Blackmon et. al. discloses and claims aqueous gel-containing topical medications comprising high concentrations of alcohol, water and topically effective amounts of a pharmaceutical active such as hydrocortisone, diphenhydramine hydrochloride, lidocaine or miconazale nitrate in a gel matrix primarily consisting of water-soluble carboxyvinyl polymers. A gel clarifying agent may be optionally added for aesthetic reasons.

U.S. Pat. No. 4,937,078 to Mezie et. al. discloses the incorporation of similar topical anesthetic actives into liposomes which essentially encapsulate the active with layers of lipid material. It is asserted that the lipid vesicles provide a more pronounced cutaneous anesthetic or analgesic effect while employing less of the topical anesthetic agent. The lipid vesicles allegedly provide a means of controlling the permeation rate without the risk for discomfort due to numbness or systemic reactions.

U.S. Pat. No. 5,081,158 to Pomerantz discloses the use of medicated protective films as a carrier for topical anesthetics. The films are comprised of hydroxypropyl cellulose (HPC) and an esterification agent which renders the HPC soluble in a non-volatile solvent such as ethanol, isopropanol or methanol. Medicinal compounds such as benzocaine, dyclonine hydrochloride and a variety of other topical anesthetics, antibiotics and steroids are incorporated which, when applied to the skin, result in situ formed medicated films from which the actives are released to provide a sustained supply of the medicine at the treatment site.

U.S. Pat. No. 5,002,974 to Geria discloses a topical anesthetic and skin moisturizing composition comprising any one of a number of topical anesthetics, including pramoxine, in an oil-in-water emulsion including a dissolved surface active agent. The composition is asserted to provide an aesthetically pleasing analgesic skin care product. The emulsion not only provides relief from the pain associated with irritated skin but is asserted to soften and moisturize the skin with an oily coating.

Finally, U.S. Pat. No. 4,493,591 to Fourman et al discloses skin care cosmetic formulations comprised of a cellulosic polymer/solvent system capable of dispersing thin, substantive films upon the skin. Such films may serve as a carrier for sun blocking agents and insect repellents and also serve to prevent water loss form the skin surface to the environment. U.S. Pat. No. 4,389,418 to Burton et. al., in a more general and traditional sense, discloses the use of hydrocarbons such as petrolatum, paraffin wax and ozokerite and other emollients as skin moisturizing materials. These function by covering the skin with a hydrophobic occlusive film which prevents water loss from the skin to the environment.

While the foregoing topical anesthetics and moisturizers possess valuable pain-killing and skin softening properties when utilized in creams and lotions, they are also generally regarded as aesthetically undesirable in that they lack good tactile properties, are visible when worn and generate a greasy, oily feel.

SUMMARY OF THE INVENTION

The present invention comprises a clear and therefore aesthetically pleasing topical anesthetic that provides immediate and up-front relief from pain and skin irritation that is not oily or greasy to the touch. More specifically, the present invention comprises the administration of the fast acting topical anesthetic pramoxine in a carrier solution that is both shelf stable and clear in color. The anesthetic is dissolved in an aqueous solution and incorporated in a cellulosic carrier which is readily dispersed therein. Fragrances, gelling agents and other additives may be incorporated to provide a pleasant smelling, clear gel or lotion if desired.

DETAILED DESCRIPTION OF THE INVENTION

Pramoxine (4-[3-(4-butoxy phenoxy)propyl]morpholine) and particularly, its hydrochloride salts, provides superior analgesic properties and is readily absorbed by the skin when used as a topical anesthetic. Its chemical structure is as follows:

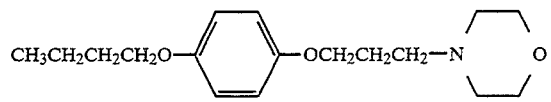

The compound is highly effective as both a topical analgesic and anesthetic and has been described in U.S. Pat. No. 2,870,151 to Abbott and its method of preparation set forth in Wright, Moore J. Am. Chem. Soc. 73 2281 (1951), both of which are hereby incorporated by reference. It has been surprisingly found that the agent may be incorporated in an aqueous system that is comprised almost entirely of water and is therefore both odorless and clear with no greasy feel or oily film to the touch. There is no need for any additional stabilizers as the medication is surprisingly shelf stable.

The topical anesthetic compositions of the present invention will generally comprise pramoxine in amounts from about 0.5% w/v to about 10% w/v based on a weight percent of the entire composition. Preferably, the anesthetic will be incorporated in amounts of from about 0.5% to about 5.0% w/v and most preferably in an amount of from about 0.75% w/v to about 1.5% w/v based on the weight of the total composition.

The pramoxine is preferably first dissolved in water together with a skin protectant such as zinc acetate, zinc oxide, mineral oil and the like. The skin protectant serves to aid in the healing process and is added in an amount from about 0.05% w/v to about 0.20% w/v and preferably in an amount of about 0.12% w/v. This mixture is then combined with a thickening agent which gives a greater degree of viscosity to the formulation and acts as a carrier for the active ingredients. This thickening agent may be selected from the group consisting of a cellulose derivatives such as hydroxypropyl methylcellulose, methyl cellulose, sodium carboxymethyl cellulose, carboxymethyl cellulose, natural gums such as carrageenan, alginate, gelatin and the like, and carbomers, carbopol and mixtures thereof. Hydroxypropyl methylcellulose is the thickening agent of choice and comprises from about 0.5% w/v to about 1.5% w/v of the weight of the total composition, and preferably from about 0.8% w/v to about 1.1% w/v. The cellulose powders are first "wetted" with water to provide a dispersion to which the pramoxine/zinc acetate solution is then added.

An emollient is also incorporated in order to moisturize and soften the skin which further aids in its healing and recovery. Suitable emollients include glycerin, propylene glycol, butylene glycol and mixtures thereof. The emollient component is added in amounts of from about 1.5% w/v to about 5.0% w/v and preferably in an amount of from about 2.0% w/v to about 3.0% w/v based on the weight of the entire formulation. Although the base composition is odorless, fragrance oils and perfumes may preferably also be added to improve the smell of the product. These must first be dissolved in an organic solvent such as ethanol, methanol and the like to increase the oils dispersion properties and equally distribute the oil throughout the cellulosic powders of the carrier thickening agent.

Emulsifiers and surfactants may be added to fully disperse the fragrance oils and the other ingredients in general. Suitable emulsifiers include diglycerides, fatty acids such as capric, myristic and oleic acid, and their salts thereof, lecithin, polyoxyethylene sorbitans such as Polysorbate 40 and mixtures thereof. The emulsifiers may be employed in amounts of from about 1.5% w/v to about 3.5% w/v based on the total weight of the anesthetic composition, and preferably will be employed from about 2.0% w/v to about 3.0% w/v by weight and most preferably in an amount of about 2.5% w/v by weight.

The present invention may additionally include other ingredients such as antioxidants, buffers, acidifiers, and other healing agents and skin softeners and the like. Compounds of this nature suitable for incorporation into formulations of the present invention are well known to those skilled in the art and may be added and blended in after the primary materials are mixed.

The following examples are presented in order to better define and set forth working embodiments of the present invention. They are for illustrative purposes only however, and should not be construed as limiting the true spirit and scope of the invention, as recited in the claims that follow. All parts and percentages set forth therein are based upon a weight percentage of the entire topical anesthetic composition.

EXAMPLE 1

The following ingredients were collected in their respective amounts.

| | Ingredients | Percent w/v | Ingredient Per Liter |
|---|---|---|---|
| 1. | Hydroxypropyl Methylcellulose 22008 | .9000 | 9.0000 gms |
| 2. | Methocel K100 | 1.5200 | 15.2000 gms |
| 3. | Pramoxine Hydrochloride USP | 1.0750 | 10.750 gms |
| 4. | Glycerin USP Special | 2.5000 | 25.0000 gms |
| 5. | Zinc Acetate Dehydrate (reagent grade) | 0.1200 | 1.2000 gms |
| 6. | Alcohol S.D. 38B | 2.0425 | 20.4250 gms |
| 7. | Perfume Oil, PA 66694 | .0245 | .2450 gms |
| 8. | Camphor USP | .0900 | .9000 gms |
| 9. | Polysorbate 40 NF | .1075 | 1.0750 gms |
| 10. | Germaben II | 1.0000 | 10.0000 gms |
| 11. | Citric Acid USP Granular (Hydrous) | .0700 | .7000 gms |
| 12. | Sodium Citrate Granular UPS | .0300 | .3000 gms |
| 13. | Purified Water USP | Q.S. | Q.S. |
| | Totals | 100.0% | 1000.0% mls |

Five liters of water were heated to about 80–90 C.° in a jacketed calibrated tank to which was added the hydroxpropyl methyl cellulose and the Methocel K100. The solution was vigorously mixed until all the cellulose powders were wetted. The mixture was then cooled to room temperature and another 100 ml. of water was placed into a second tank to which was mixed the pramoxine hydrochloride, the zinc acetate dihydrate, the citric acid and the sodium citrate under slow speed mixing. The first mixture was then added to the second under moderate mixing speed while the alcohol, perfume, polysorbate 40 and camphor were combined in a third vessel. These components were then blended until a homogenous mixture was obtained. The third mixture and the Germaben II were all mixed in the main kettle which was brought to full volume by adding the remainder of the water. The components were fully mixed until a smooth, thick, clear homogenous solution was obtained.

What we claim is:

1. An improved clear liquid topical anesthetic composition for the relief of pain and irritation comprising:
   a) Hydroxypropyl Methylcellulose, wherein said Hydroxypropyl Methylcellulose is present in an amount of from about 1.0% w/v to about 3.5% w/v;
   b) Pramoxine Hydrochloride, wherein said Pramoxine Hydrochloride is present in an amount of from about 0.5% w/v to about 10% w/v;
   c) Glycerin, wherein said Glycerin is present in an amount of from about 1.0% w/v. to about 5.0%w/v;
   d) Zinc Acetate Dihydrate, wherein said Zinc Acetate is present in an amount of from about 0.05% w/v to about 2.0% w/v;
   e) Alcohol, wherein said Alcohol is present in an amount of from about 0.5% w/v to about 10% w/v;
   f) Perfume Oil, wherein said Perfume Oil is present in an amount of from about 0.0020% w/v to about 0.2% w/v;
   g) Camphor, wherein said Camphor is present in an amount of from about 0.0010% w/v to about 1.0% w/v;
   h) Polyoxyethylene Sorbitan, wherein said Polyoxyethylene Sorbitan is present in an amount of from about 0.01% w/v to about 10% w/v;

i) Mixture of propylene glycol, diazolidinyl urea, methylparaben and propylparaben, wherein said Mixture is present in an amount of from about 0.1% w/v to about 3% w/v;

j) Citric Acid, wherein said Citric Acid is present in an amount of from about 0.007% w/v to about 1% w/v;

k) Sodium Citrate, wherein said Sodium Citrate is present in an amount of from about 0.003% w/v to about 1% w/v; and l) Purified Water.

2. The improved topical anesthetic of claim 1 in an clear, non-oily aqueous carrier lotion.

3. The improved topical anesthetic of claim 1 in a clear, non-oily gel.

4. The improved topical anesthetic of claim 1 in a clear aerosol or pump spray.

5. A method for treatment of skin irritation and pain due to insect bites, burn, allergic rash comprising the topical application of the composition of claim 1 to the affected area.

6. The anesthetic composition according to claim 1 for the relief of pain and irritation comprising:

| Ingredients | Percent (w/v) |
|---|---|
| a) Hydroxypropyl Methylcellulose | 2.4200 |
| b) Pramoxine Hydrochloride | 1.0750 |
| c) Glycerin | 2.5000 |
| d) Zinc Acetate Dihydrate | 0.1200 |
| e) Alcohol | 2.0425 |
| f) Perfume Oil | 0.0245 |
| g) Camphor | 0.0900 |
| h) Polyoxyethylene Sorbitan | 0.1075 |
| i) Mixture of<br>  1) propylene glycol<br>  2) diazolidinyl urea<br>  3) methylparaben<br>  4) propylparaben | 1.0000 |
| j) Citric Acid | 0.0700 |
| k) Sodium Citrate | 0.0300 |
| l) Purified Water | Q.S. |

\* \* \* \* \*